US006156913A

United States Patent [19]
Hyatt

[11] Patent Number: 6,156,913
[45] Date of Patent: Dec. 5, 2000

[54] METHOD OF PRODUCING VITAMIN E

[75] Inventor: John Anthony Hyatt, Kingsport, Tenn.

[73] Assignee: Eastman Chemical Company, Kingsport, Tenn.

[21] Appl. No.: 09/347,769

[22] Filed: Jul. 6, 1999

Related U.S. Application Data

[60] Provisional application No. 60/091,868, Jul. 6, 1998.
[51] Int. Cl.$^7$ ...................... C07D 311/72; C07D 303/22; C07D 33/04
[52] U.S. Cl. .......................... 549/408; 549/411; 549/554; 568/873; 568/874
[58] Field of Search ................................... 549/408, 411, 549/554; 568/873, 874

[56] References Cited

U.S. PATENT DOCUMENTS

| | | | |
|---|---|---|---|
| 3,862,988 | 1/1975 | Pond et al. | 260/593 R |
| 3,917,710 | 11/1975 | Pond et al. | 260/593 R |
| 4,305,876 | 12/1981 | Barner et al. | 260/343.6 |
| 5,349,097 | 9/1994 | Thome et al. | 568/906 |

FOREIGN PATENT DOCUMENTS

| | | |
|---|---|---|
| 209158 A2 | 1/1987 | European Pat. Off. . |
| 0 283 946 | 9/1988 | European Pat. Off. . |
| 24 04 621 | 7/1975 | Germany . |
| 61-236737 A2 | 10/1986 | Japan . |
| 63-063674 A2 | 3/1988 | Japan . |
| 63-179850 A2 | 7/1988 | Japan . |
| WO 9421595 A1 | 9/1994 | WIPO . |

OTHER PUBLICATIONS

B. Stalla–Bourdillon, "Mises Au Point Sur Les Syntheses de la Vit. E," Ind. Chim. Bel., vol. 35, pp. 13–25 (Jan. 1970).
Sato, et al. "Preparation of Optically Active α–tocopherols," Chem. Abstract, vol. 110, p. 688 (1989).
S. Kasperek, "Chemistry of Tocopherols and Tocotrienols" Chapter 2, pp. 8–65. L. Machlin, ed, "Vitamin E: A Comprehensive Treatise", Marcel Dekker, NY, 1980.
T.W. Green, "Protective Groups in Organic Synthesis" pp. 10–86, John Wiley and Sons, 1981.
Schmidt, J.Prakt. Chem./Chem Ztg. 339, 493 (1997).
Z.Zhu, J.H. Espenson, "Organic Reactions Catalyzed by Methylrhenium Trioxide: Dehydration, Amination, and Disporportionation of Alcohols" J.Org. Chem. 61, 324 (1996).
Z. Zhu, J.H. Espenson, "Methylrhenium Trioxide As A Catalyst For Oxidations With Molecular Oxygen And For Oxygen Transfer" J.Mol.Catalysis A,Chemical, 103, 87 (1995).
K.B. Sharpless, R.C. Michaelson, "High Stereo and Regioselectivities In The Transition Metal Catalyzed Epoxidations Of Olefinic Alcohols by tert–Butyl Hydroperoxide" J.Amer.Chem.Soc. 95, 6136 (1973).

J.G. Hill, B.E. Rossiter, K.B. Sharpless, "Anhydrous tert-–Butyl Hydroperoxide in Toluene: The Preferred Reagent for Applications Requiring Dry TBHP", J.Org.Chem. 48, 3607 (1983).
"Vitamin E", vol. 24, pp. 214–255, Kirk Othmer Encyclopedia of Chemical Technology, 3d Ed. 1984 John Wiley and Sons.
Sata, et al., "Tetrahedron Lett. 40(4), 719 (1999) (abstract only).
Rontani et al., Phytochemistry 42(2) 347 (1996) (abstract only).
Rontani et al., J.Photochem. Photobiol.A. 79(3) 167 (1994) (abstract only).
B.C. Pearce, et al, "Inhibitors of Cholesterol Biosynthesis. 2. Hypocholesterolemic and Antioxidant Activities of Benzopyran and Tetrahydronaphthalene Analogues of the Tocotrienols", Journal of Medicinal Chemistry, vol. 37, No. 4, pp. 526–541 (1994).
Rontani et al., J.Photochem. Photobiol.A. 79(3) 167 (1994) (abstract only).
Rontani et al., J.Photochem. Photobiol.A. 85(1–2)137 (1995) (abstract only).
Rontani et al., Tetrahedron Lett. 32(45), 6551 (1991) (abstract only).
J. Muzart, Tetrahedron Lett. 28(19) 2133 (1987) (abstract only).
Aliya et al., Pak J. Mar. Sci. 3(1) 15 (1994) (abstract only).

*Primary Examiner*—Ba K. Trinh
*Attorney, Agent, or Firm*—Cheryl J. Tubach; Harry J. Gwinnell

[57] ABSTRACT

The invention provides processes for producing phytol, isophytol, and certain phytol derivatives by a method of oxidizing or epoxidizing geranylgeraniol or geranylgeraniol derivatives to form epoxygeranylgeraniol derivatives, reducing or hydrogenating the epoxygeranylgeraniol derivatives to produce epoxyphytol derivatives, and then deoxygenating the epoxyphytol derivatives to produce phytol, isophytol, phytene derivatives, isophytene derivatives, or mixtures thereof. The step of deoxygenating is carried out in the presence of deoxygenation catalysts, including rhenium trioxide compounds. The invention also provides methods for the synthesis of certain novel substituted epoxyphytyl compounds and substituted phytene compounds having removable protecting groups. The produce phytol, isophytol, phytene derivatives, isophytene derivatives, substituted epoxyphytyl compounds and substituted phytene compounds are suitable starting materials for condensation with trimethylhydroquinone derivatives in the presence of Lewis acids to give tocopherol derivatives including alpha-tocopherol, vitamin E.

51 Claims, No Drawings

METHOD OF PRODUCING VITAMIN E

CROSS REFERENCE TO RELATED APPLICATIONS

This application claims priority to U.S. Provisional Application Ser. No. 60/091,868, entitled "Method of Vitamin Production", filed Jul. 6, 1998.

FIELD OF THE INVENTION

This invention relates generally to processes for producing phytol, isophytol, certain phytol derivatives, vitamin E, and related tocopherol derivatives including alpha-tocopherol.

BACKGROUND OF THE INVENTION

Vitamin E (d-alpha-tocopherol, 1) is an important nutritional supplement in humans and animals. Compound 1 is obtained commercially by isolation from a variety of plant oils, or semi-synthetically by ring methylation of the related naturally occurring d-gamma-tocopherol 2. A more important source of vitamin E is total synthesis, which provides synthetic vitamin E, d,l-alpha-tocopherol, 3. Although a mixture of isomers, 3 provides much of the biological activity of 1 and is widely used due to its lower cost and greater availability. For a general discussion of vitamin E, see L. Machlin, ed., "Vitamin E: A Comprehensive Treatise", Marcel Dekker, NY, 1980.

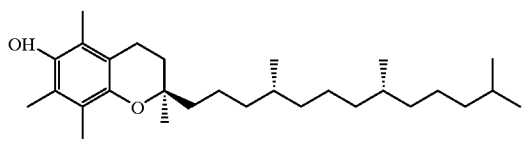

1

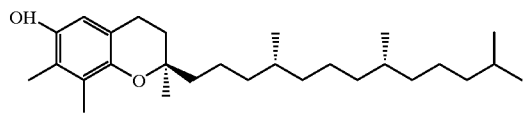

2

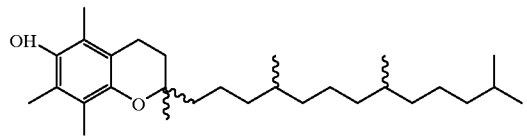

3

The mixture of isomers comprising synthetic vitamin E, d,1-alpha-Tocopherol 3, is typically obtained by reacting trimethylhydroquinone 4 with either phytol 5 or isophytol 6 in the presence of an acid catalyst, often a Lewis acid such as zinc chloride.

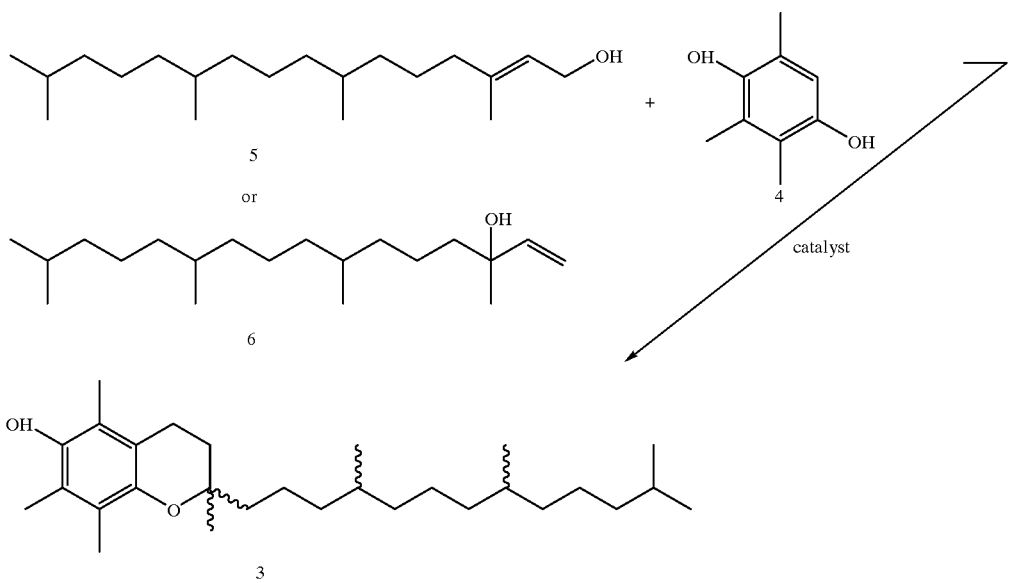

This technology was reviewed by S. Kasparek in L. Machlin, ed., Vitamin E: A Comprehensive Treatise, chapter 2, pp. 8–65, Marcel Dekker, NY, 1965. References 140–166 of this chapter provide the primary references to detailed methods of preparing compound 3.

The phytol 5 or isophytol 6 required for the prior art preparations of 3 have typically been obtained through multi-step synthesis. Starting materials typically included acetone (see Kasparek, in Machlin, Vitamin E: A Comprehensive Treatise, pp. 44–45, Dekker, NY 1980, and references cited therein) and cyclic isoprene trimer (Pond et al., U.S. Pat. Nos. 3,917,710 and 3,862,988 (1975).

One embodiment of the present invention relates to methods for preparing phytol, isophytol, certain substituted derivatives thereof, and vitamin E, starting from geranylgeraniol 7.

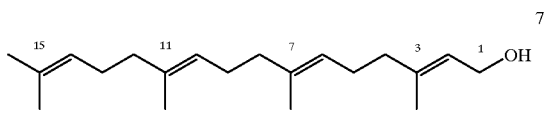

7

Geranylgeraniol can be derived from plant or microbial sources, but at high cost. More economical techniques for production and isolation of geranylgeraniol can be provided by modern biotechnology, as disclosed in U.S. Provisional Application Ser. No. 60/091,686, incorporated herein by reference.

The present invention further relates to certain $C_{20}$ epoxide derivatives, such as 2,3-epoxygeranylgeraniol, 8, 2,3-epoxyphytol 9, and 1,2-epoxyisophytol, 10. Compounds 8, 9, and 10 are known (Sata et.al., *Tetrahedron Letters* 1999, 40(4) 719–722;

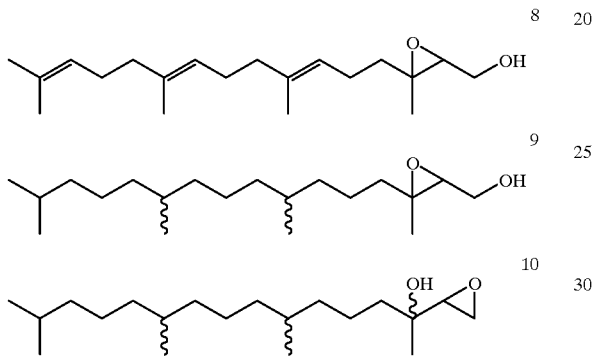

and Sato et.al, JP 63063674, A2 880302; Rontani et.al., *Phytochemistry*, 1996, 42(2), 347–351; Aliya et.al, *Pak J. Mar. Sci.* 1994, 3(1), 15–24; Rontani et.al., *J. Photochem. Photobiol. A* 1994, 79(3), 167–172; Kanehira et.al., JP 63179850 A2 880723;).

Methods are also known in the art for selectively epoxidizing the carbon—carbon double bond of allylic alcohols in the presence of other carbon—carbon double bonds, by utilizing t-butyl-hydroperoxide in the presence of molybdenum or vanadium catalysts (Sharpless et.al., *J.Amer.Chem. Soc.* 1973, 95,6136–6137). Those methods have been applied to synthesize 1,2-epoxyisophytol, 10, from isophytol, 6 (Mori et.al., abstract of JP 61236737 A2 861022)

In the last few years, a rhenium compound, $CH_3ReO_3$, methyl rhenium trioxide, 11, has been shown to be a useful catalyst for a variety of transformations of organic compounds, as reviewed by Schmidt (*J. Prakt. Chem./Chem Ztg.* 1997, 339, 493–496). The types of reactions catalyzed by $CH_3ReO_3$ include the isomerization and/or equilibration of allylic alcohols such as phytol (U.S. Pat. No. 5,349,097 to Tome et.al.), the dehydration of primary alcohols to give ethers and olefins (Zhu and Espenson, *J.Org. Chem.* 1996, 61, 324–328) and the deoxygenation of epoxides in the presence of oxygen acceptors to give olefins (Zhu and Espenson,*J. Mol. Catalysis A: Chemical* 1995, 103, 87–94).

Despite the various known methods for preparing or isolating members of the vitamin E family of compounds and their precursors, there remains a need for improved and more efficient methods of production of phytol, isophytol, and Vitamin E. It would be especially useful to chemically convert geranylgeraniol 7 to phytol 5, isophytol 6, vitamin E, or related compounds.

SUMMARY OF THE INVENTION

In some of its aspects, the invention provides methods for preparing phytol, isophytol, and related compounds.

In one embodiment, the invention provides a general method comprising the steps of:

(a) oxidizing geranylgeraniol or a geranylgeraniol derivative to produce an epoxy-geranylgeraniol derivative;

(b) reducing the epoxy-geranylgeraniol derivative to produce an epoxyphytyl derivative; and (c) deoxygenating the epoxyphytyl derivative in the presence of at least one oxygen acceptor;

to produce phytol, a phytene derivative, isophytol, an isophytene derivative, or a mixture thereof.

In another aspect, the invention provides novel substituted epoxyphytyl compounds of the structure

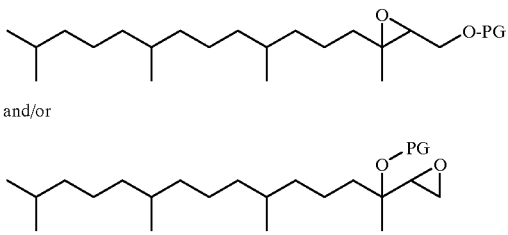

and/or wherein PG is a removable protecting group.

The invention also provides novel substituted phytene compounds of the structure

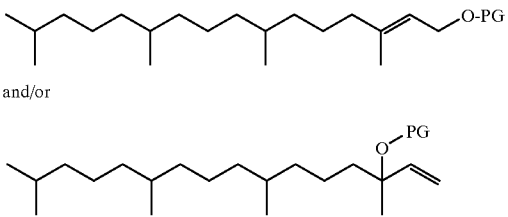

and/or wherein PG is a removable protecting group.

In one aspect, the invention provides methods for producing the substituted phytene compounds, by deoxygenating the substituted epoxyphytyl compounds, in the presence of at least one oxygen acceptor and at least one deoxygenation catalyst, under conditions and for a time sufficient to produce at least some of a substituted phytene compound.

In other aspects, the invention relates to methods for producing alpha-tocopherol.

In one general embodiment, the invention provides a method for producing alpha-tocopherol comprising the steps of:

(a) providing an epoxyphytyl derivative;

(b) deoxygenating the epoxyphytyl derivative in the presence of an oxygen acceptor and a deoxygenation catalyst to produce phytol, a phytene derivative, isophytol, an isophytene derivative, or a mixture thereof; and (c) condensing the phytol, phytene derivative, isophytol, isophytene derivative, or a mixture thereof with trimethylhydroquinone;

to produce alpha-tocopherol.

In one specific aspect, the invention provides a method for converting geranylgeraniol to alpha-tocopherol, comprising the steps of:

(a) epoxidizing geranylgeraniol in the presence of an organic hydroperoxide and a molybdenum or vanadium catalyst, to produce 2,3-epoxy-geranylgeraniol;

(b) hydrogenating 2,3-epoxy-geranylgeraniol in the presence of a hydrogenation catalyst to produce 2,3-epoxyphytol;

(c) deoxygenating 2,3-epoxyphytol in the presence of a phosphine and $CH_3$—$ReO_3$, to produce phytol, isophytol, or mixtures thereof; and (d) condensing trimethylhydroquinone with phytol, isophytol, or mixtures thereof, in the presence of a Lewis acid catalyst;

to produce alpha-tocopherol.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION OF THE PREFERRED EMBODIMENTS

The present invention may be understood more readily by reference to the following detailed description of preferred embodiments of the invention and the examples included therein.

Definitions and Use of Terms

Before the present compounds, compositions and methods are disclosed and described, it is to be understood that the terminology used herein is for the purpose of describing particular embodiments only and is not intended to be limiting.

It must be noted that, as used in the specification and the appended claims, the singular forms "a," "an" and "the" include plural referents unless the context clearly dictates otherwise. Thus, for example, reference to "an aromatic compound" includes mixtures of aromatic compounds, reference to "a pharmaceutical carrier" includes mixtures of two or more such carriers, and the like.

Ranges are often expressed herein as from "about" one particular value, and/or to "about" another particular value. When such a range is expressed, another embodiment includes from the one particular value and/or to the other particular value. Similarly, when values are expressed as approximations, by use of the antecedent "about", it will be understood that the particular value forms another embodiment. It will be further understood that the endpoints of each of the ranges are significant both in relation to the other endpoint, and independently of the other endpoint.

Optional or optionally means that the subsequently described event or circumstance may or may not occur, and that the description includes instances where said event or circumstance occurs and instances where it does not. For example, the phrase optionally substituted lower alkyl means that the lower alkyl group may or may not be substituted and that the description includes both unsubstituted lower alkyl and lower alkyl where there is substitution.

In this specification and in the claims which follow, reference will be made to a number of terms which shall be defined to have the following meanings:

The term "alkyl" as used herein refers to a branched or unbranched saturated hydrocarbon group of 1 to 24 carbon atoms, such as methyl, ethyl, n-propyl, isopropyl, n-butyl, isobutyl, t-butyl, octyl, decyl, tetradecyl, hexadecyl, eicosyl, tetracosyl and the like. Preferred alkyl groups herein contain from 1 to 12 carbon atoms. The term "lower alkyl" intends an alkyl group of from one to six carbon atoms, preferably from one to four carbon atoms. The term "cycloalkyl" intends a cyclic alkyl group of from three to eight, preferably five or six carbon atoms.

The term "alkoxy" or "alkoxide" as used herein intends an alkyl group bound through a single, terminal ether linkage; that is, an "alkoxy" or "alkoxide" group may be defined as —OR where R is alkyl as defined above. A "lower alkoxy" group intends an alkoxy group containing from one to six, more preferably from one to four, carbon atoms.

The term "alkylene" as used herein refers to a difunctional saturated branched or unbranched hydrocarbon chain containing from 1 to 24 carbon atoms, and includes, for example, methylene (—$CH_2$—), ethylene (—$CH_2$—$CH_2$—), propylene (—$CH_2$—$CH_2$—$CH_2$—), 2-methylpropylene [—$CH_2$—$CH(CH_3)$—$CH_2$—], hexylene [—$(CH_2)_6$—] and the like. "Lower alkylene" refers to an alkylene group of from 1 to 6, more preferably from 1 to 4, carbon atoms. The term "cycloalkylene" as used herein refers to a cyclic alkylene group, typically a 5- or 6-membered ring.

The terms "alkene" or "olefin" as used herein intends a carbon-containing compound or functional group of 2 to 24 carbon atoms having 1 to 4 carbon—carbon double bonds, excluding any carbon—carbon double bonds which are part of an aromatic ring. Preferred alkene or olefin groups within this class contain 2 to 12 carbon atoms. Asymmetric structures such as (AB)C=C(CD) are intended to include both the E and Z isomers. This may be presumed in structural formulae herein wherein an asymmetric alkene is present, or it may be explicitly indicated by the bond symbol =.

The term "alkanol" is used to represent $C_1$–$C_{20}$ straight, branched chain, or cyclic alcohols, and mono-ethers of ethylene glycol or propylene glycol, having straight or branched chain $C_1$–$C_4$ alkyl ether groups. The term "ether" includes compounds of the formula $R_x$—O—$R_y$, wherein $R_x$ and $R_y$ are $C_1$–$C_{10}$ alkyl or aryl groups, and tetrahydrofuran.

The term "catalyst" is defined as any compound or compositions which accelerates or improves the rate or selectivity of a chemical reaction without substantial consumption of the catalyst compound or composition.

A protecting group (PG) is defined for the purposes of this invention as a substituent group which can be chemically bound to an oxygen atom, and subsequently removed (either chemically, in-vitro, or in-vivo) from the oxygen atom by predictable methods. Examples of many of the possible protective groups can be found in *Protective Groups in Organic Synthesis* by T. W. Green, John Wiley and Sons, 1981, pp. 10–86, which is incorporated herein by reference in its entirety.

The term "oxidizing" is defined to encompass any reaction or sequence of reactions which substantially removes electrons from a chemical substance, or any functional group or chemical bond thereof. Oxidizing need not involve oxygen atoms, or transfer of oxygen atoms.

The term "oxidizing agent" is defined to include any compound which receives electrons from an oxidizable substrate, bond, or functional group. Oxidizing agents need not contain, receive, or donate oxygen atoms.

The term "reducing" is defined for the purposes of this invention as a process of transferring or donating one or more electrons to a chemical compound or composition. A reducing agent is defined for the purposes of this invention as any device, chemical compound, or composition which is capable of donating or transferring one or more electrons to another chemical compound or composition. A reducing agent may or may not also donate hydrogen nucleii to the other chemical composition.

A hydrogen donor is defined for the purposes of this invention as a chemical compound or composition which is capable of donating or transferring a hydrogen nucleus to a chemical compound or composition which is being reduced. A hydrogen donor may or may not also donate electrons to the chemical compound or composition. The hydrogen donors may donate or transfer the hydrogen nuclei to another chemical compound or composition in association with various numbers of electrons (including acidic hydrogen, $H^+$, with no associated electrons; neutral hydrogen, as $H^{\cdot}$, H-Donor, or $H_2$, wherein the donor provides approximately one associated electron per hydrogen nucleus; or as hydridic hydrogen, $H^-$, having approximately two associated electrons per hydrogen nucleus).

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —$OCH_2CH_2O$— units in the polyester, regardless of whether ethylene glycol was used to prepare the polyester. Similarly, a phenolic residue in a compound refers to one or more aryl groups having an oxygen singly bonded to a carbon atom which is part of an aryl ring, regardless of whether the residue is obtained by reacting phenol or an ester thereof to obtain the compound.

References in the specification and concluding claims to parts by weight, of a particular element or component in a composition or article, denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent of a component, unless specifically stated to the contrary, is based on the total weight of the formulation or composition in which the component is included.

By the term "effective amount" of a compound or property as provided herein is meant such amount as is capable of performing the function of the compound or property for which an effective amount is expressed. As will be pointed out below, the exact amount required will vary from process to process, depending on recognized variables such as the compounds employed and the processing conditions observed. Thus, it is not possible to specify an exact "effective amount." However, an appropriate effective amount may be determined by one of ordinary skill in the art using only routine experimentation.

Discussion

In certain embodiments, the invention provides a general method for preparing phytol, isophytol, and related compounds comprising the steps of:

(a) oxidizing geranylgeraniol or a geranylgeraniol derivative to produce an epoxy-geranylgeraniol derivative;

(b) reducing the epoxy-geranylgeraniol derivative to produce an epoxyphytyl derivative; and (c) deoxygenating the epoxyphytyl derivative in the presence of at least one oxygen acceptor;

to produce phytol, a phytene derivative, isophytol, an isophytene derivative, or a mixture thereof.

The Chemical Compounds

Geranylgeraniol, 7, is a preferred starting material for the instant invention. Nevertheless, a variety of other geranylgeraniol derivatives can serve as starting materials. A geranylgeraniol derivative is defined for the purposes of this invention as a compound having the $C_{20}$-3,7,11,15-tetraalkyl skeleton of geranylgeraniol; i.e.,

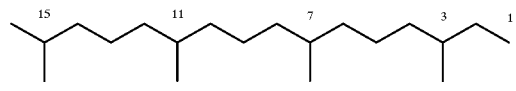

at least two carbon—carbon double bonds, and at least one heteroatom or heteroatom substituent group bound at the 1- or 3-positions. Otherwise, geranylgeraniol derivatives may have different patterns of hydrogen or other substituents than geranylgeraniol. The heteroatom may comprise any element other than carbon or hydrogen, including oxygen, sulfur, halides, nitrogen, metals, and the like. The heteroatom bonded at the 1- or 3-position of the geranylgeraniol derivative may also be bonded to other atoms or substituent groups, to form heteroatom substituent groups. Oxygen is a preferred heteroatom, and hydroxy groups are preferred heteroatom substituent groups.

Step (a) of the above-described method produces an epoxy-geranylgeraniol derivative. An epoxy-geranylgeraniol derivative is defined for the purposes of this invention as any compound having the $C_{20}$-3,7,11,15-tetralkyl skeleton of geranylgeraniol, with at least one carbon—carbon double bond, and at least one three-membered epoxide ring, wherein the epoxide oxygen bridges carbons 1 and 2, or carbons 2 and 3. The epoxy-geranylgeraniol derivatives also have a heteroatom or heteroatom substituent group bound at the 1- or 3-position which is not bridged with the epoxide ring. Oxygen is a preferred heteroatom, and hydroxy groups are preferred heteroatom substituent groups. Otherwise, epoxy-geranylgeraniol derivatives may have different patterns of hydrogen, oxygen, or heteroatomic substituents than geranylgeraniol.

Preferred epoxy-geranylgeraniol derivatives include 2,3-epoxy-geranylgeraniol (compound 8), and 1,2-epoxy-geranylgeraniol, which has the following structure.

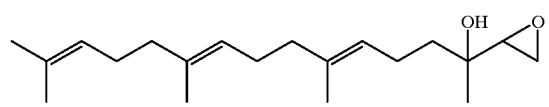

Those skilled in the art will recognize that these preferred compounds can be reacted with protecting group precursors, to produce substituted epoxy-geranylgeraniol derivatives of the structure:

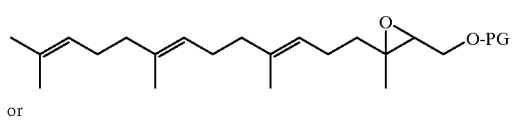

or

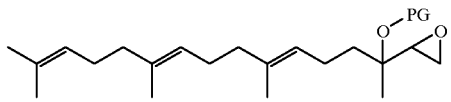

wherein PG is a removable protecting group.

Preferred protecting groups include acyl groups derived from $C_2$–$C_{20}$ carboxylic acids. When the acyl group of a carboxylic acid is bonded to the oxygen atom of an epoxy-geranylgeraniol derivative, a $C_2$–$C_{20}$ ester protecting group is formed. Acetate ester groups are particularly preferred. Substituted epoxy-geranylgeraniol derivatives having protecting groups are suitable substrates for subsequent steps of the method.

Step (b) of the above-described produces an epoxyphytyl derivative. An epoxyphytyl derivative is defined for the purposes of this invention as a compound having the $C_{20}$-3,7,11,15-tetraalkyl skeleton of geranylgeraniol, at least one three-membered epoxide ring, wherein the epoxide oxygen bridges carbons 1 and 2, or carbons 2 and 3, and having no carbon—carbon double bonds. The epoxy-phytyl derivatives also have heteroatom or heteroatom substituent group bound at the 1- or 3-position which is not bridged with the epoxide ring. Oxygen is a preferred heteroatom, and hydroxy groups are preferred heteroatom substituent groups. Otherwise, epoxyphytyl derivatives may have different patterns of hydrogen, oxygen, or heteroatomic substituents than geranylgeraniol, phytol, or isophytol.

Preferred epoxyphytyl derivatives include 2,3-epoxyphytol, compound 9; 1,2-epoxy-isophytol, compound 10; and substituted epoxyphytyl compounds of the formula:

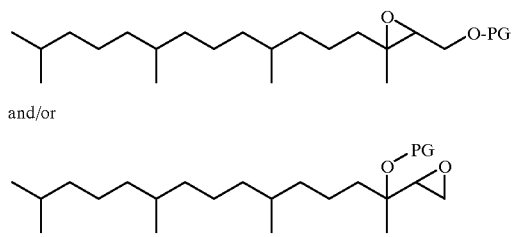

and/or wherein PG is a removable protecting group.

Step (c) of the above-described method produces phytol, a phytene derivative, isophytol, an isophytene derivative, or a mixture thereof. Phytene derivatives are defined for the purposes of this invention as compounds having the same $C_{20}$-3,7,11,15-tetraalkyl carbon-hydrogen skeleton as geranylgeraniol, a $C_2$–$C_3$ carbon—carbon double bond, and a heteroatom or heteroatomic substituent group at the 1-carbon. Isophytene derivatives are defined for the purposes of this invention as compounds having the $C_{20}$-3,7,11,15-tetraalkyl carbon-hydrogen skeleton of geranylgeraniol, a $C_1$–$C_2$ double bond, and a heteroatom or heteroatomic substituent group at the 3-carbon. Oxygen is a preferred heteroatom, and hydroxy groups are preferred heteroatom substituent groups.

The class of phytene derivatives include novel substituted phytene compounds having the formula:

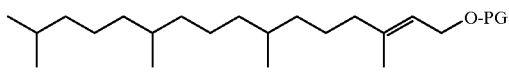

The class of isophytene derivatives include novel substituted isophytene compounds having the formula:

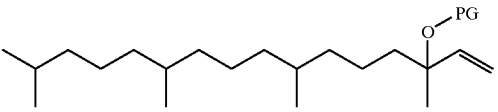

wherein PG is a removable protecting group.

Step (a)—Oxidation

Step (a) of the above-described method comprises oxidizing geranylgeraniol or a geranylgeraniol derivative to produce an epoxy-geranylgeraniol derivative. The step of oxidizing encompasses any process which converts a geranylgeraniol derivative to an epoxy-geranylgeraniol derivative. The step of oxidizing encompasses multi-step processes which oxidize a geranylgeraniol derivative to form an intermediate compound or compounds (either transient or stable) which are subsequently converted to an epoxy-geranylgeraniol derivative.

The step of oxidizing is carried out in the presence of at least one oxidizing agent, which removes electrons. Examples of classes of suitable oxidizing agents include alkyl viologen salts, trityl salts, organic and inorganic peroxy compounds, $C_1$–$C_{20}$ organic hydroperoxide compounds, $C_1$–$C_{20}$ organic peracid compounds, elemental halogens, hypohalous acids, molecular oxygen, alkyl and aryl iodosyl compounds, $C_1$–$C_{20}$ N-alkyl-morpholine oxides, compounds having metals in high oxidation states, and the like.

In a preferred embodiment of the above-described method, the oxidizing of step (a) comprises epoxidizing in the presence of at least one epoxidation catalyst. Epoxidizing is defined as a chemical reaction which results in insertion of an oxygen atom into a carbon—carbon double bond, to form a three membered ring having two carbon atoms and one oxygen atom. Epoxidation catalysts accelerate or improve the selectivity of epoxidation reactions. A preferred class of epoxidation catalysts comprise transition metals, lanthanide, or actinide metal compounds having metal-oxide bonds. Highly preferred epoxidation catalysts comprise vanadium or molybdenum compounds.

In embodiments involving epoxidation, the step of epoxidizing is carried out in the presence of an epoxidizing agent, which donates an oxygen atom. Preferred classes of epoxidizing agents include but are not limited to organic or inorganic peroxy compounds, $C_1$–$C_{20}$ organic hydroperoxide compounds, $C_1$–$C_{20}$ organic peracid compounds, and $C_1$–$C_{20}$ alkyl or aryl iodosyl compounds. Hydrogen peroxide, t-butyl-hydroperoxide, and cumene hydroperoxide are the most preferred epoxidizing agents.

The oxidizing can be carried out in the absence of solvent, but in alternative embodiments the oxidizing is carried out in the presence of at least one solvent, or mixtures of solvents. Preferred classes of $C_1$–$C_{20}$ solvents for epoxidation reactions are aromatic hydrocarbons, aliphatic hydrocarbons, cycloaliphatic hydrocarbons, or aliphatic esters. Preferred aromatic hydrocarbons include benzene, and benzenes substituted with one to three $C_1$–$C_4$ alkyl groups, such as toluene, xylenes, cumene, and the like. Preferred aliphatic hydrocarbons are straight or branched chain alkanes having five to eight carbon atoms, such as pentanes, hexanes, heptanes, and octanes. Preferred cycloaliphatic hydrocarbons include $C_5$–$C_8$ cylcloalkanes having one or more $C_1$–$C_4$ alkyl substituent groups. Cyclohexane is a preferred cycloaliphatic hydrocarbon. Aliphatic esters include compounds of the formula $R_1CO_2R_2$, wherein $R_1$ and $R_2$ independently represent a straight or branched chain $C_1$–$C_4$ alkyl group. Ethyl acetate is the most preferred aliphatic ester.

Step B—Reduction

Step B of the above-described general method for preparing phytol, isophytol, and related compounds comprises a step of reducing an epoxy-geranylgeraniol derivative to produce an epoxyphytyl derivative. In the reducing step, two electrons are added to at least one carbon—carbon double bond of the epoxy-geranylgeraniol derivative reduced. The electrons may be added simultaneously, or sequentially. When more than one carbon—carbon double bond is reduced, the carbon—carbon double bonds may be reduced concurrently or sequentially, and the same method or a different method of reduction may be used for each double bond reduced. Preferably, all the carbon—carbon bonds of the epoxy-geranylgeraniol derivative are concurrently reduced in a single reactor by a single reduction method.

The electrons for the reducing step are provided by a reducing agent. Subsequent to or concurrently with the addition of electrons to a carbon—carbon double bond, a hydrogen nucleus is also added to each carbon atom of the carbon—carbon double bonds, to form new carbon—hydrogen bonds. The required hydrogen nucleii are provided by a hydrogen donor. The hydrogen donor may or may not also function as the reducing agent, to supply the required electrons. In many embodiments, the hydrogen donor supplies electrons for the reduction step, and therefore simultaneously functions as a reducing agent. If the hydrogen donor does not supply electrons for the reduction step, a separate reducing agent must be provided to supply electrons for the reducing step. A plurality of reducing agents, or hydrogen donors, or mixtures of reducing agents and hydrogen donors can be utilized. More preferably, the reducing occurs in the presence a single hydrogen donor, which also supplies electrons, and therefore no separate reducing agent is required.

In a preferred embodiment of Step (b), the reducing comprises hydrogenating in the presence of a hydrogenation catalyst and a hydrogen donor. A step of hydrogenating is defined for the purposes of this invention as a step of reducing involving transfer of hydrogen nucleii and/or electrons from the hydrogenation catalyst to the carbon—carbon double bonds of an epoxy-geranylgeraniol derivative, so as to form new carbon-hydrogen single bonds.

In a highly preferred embodiment, the hydrogenation catalyst comprises Raney nickel, palladium on carbon, platinum on carbon, or platinum oxide. As is known in the art, each of these types of catalysts may or may not contain small quantities of modifier or promoter materials, such as another transition metal, sulfur or halide compounds.

In other embodiments of the step of reducing, the hydrogenation catalyst comprises at least one transition metal, transition metal salt, transition metal complex, or a mixture thereof. In preferred embodiments, the transition metal, transition metal salt, or transition metal complex comprises chromium, molybdenum, tungsten, manganese, rhenium, iron, ruthenium, osmium, cobalt, rhodium, iridium, nickel, palladium, platinum, or copper.

In alternative embodiments, the transition metal, transition metal salt, or transition metal complex of the hydrogenation catalyst is disposed on the surfaces of a support material. In such a supported hydrogenation catalyst, the transition metal, transition metal salt, or transition metal complex comprises from about 0.1 to about 10 weight percent of the catalyst. Preferred support materials comprise carbon, charcoal, silica, alumina, titania, zirconia, a zeolite, barium sulfate, or calcium sulfate.

Hydrogenation catalysts are typically present in a quantity of from about 0.001 to about 10 weight percent based on the starting weight of epoxy-geranylgeraniol. Preferably, the hydrogenation catalysts are present in a concentration from about 0.05 to about 5%.

The hydrogen donor for hydrogenation reactions need not comprise $H_2$. In fact, it is known in the art that carbon—carbon double bonds can be reduced via "transfer hydrogenation" reactions. Transfer hydrogenations do not employ $H_2$ as a hydrogen donor. A variety of hydrogen donors for transfer hydrogenation reactions are known, which include but are not limited to hydrazine, alcohols, and silanes.

The most preferred hydrogen donor is $H_2$, i.e. hydrogen gas. The $H_2$ can be present at a pressure from about 1 atmosphere to about 200 atmospheres. Preferably, $H_2$ is present at a pressure from about 1 atmosphere to about 75 atmospheres. Most preferably, $H_2$ is present at a pressure from about 5 atmospheres, to about 50 atmospheres.

Reduction reactions employing highly reactive reducing agents and/or hydrogen donors, such as boranes or silanes, may be carried out below ambient temperatures, including temperatures as low as $-78°$ C., or as high as $250°$ C. When the step of reducing comprises hydrogenating, the hydrogenation is typically conducted at a temperature from about $0°$ C. to about $150°$ C. Preferably, hydrogenations are conducted at a temperature from about $20°$ C. to about $100°$ C.

The steps of reducing or hydrogenating can be performed in the absence of solvent, or in the presence of at least one solvent. Suitable hydrogenation solvents include aliphatic esters, aromatic hydrocarbons, aliphatic and cycloaliphatic hydrocarbons, alkanols, or ethers.

Step C—Deoxygenating

Step C of the above-described general method comprises a step of deoxygenating an epoxyphytyl derivative in the presence of an oxygen acceptor. The term "deoxygenating" is defined for the purposes of this invention as a process in which an epoxide oxygen atom bridging two carbon atoms is removed and replaced by a carbon—carbon double bond.

An oxygen acceptor is defined for the purposes of this invention as (1) any chemical compound or composition which is capable of chemically binding or abstracting oxygen atoms from an epoxyphytol derivative, or (2) any device or process which effectively removes or consumes oxygen atoms produced by the step of deoxygenating an epoxyphytol derivative. Examples of classes of preferred oxygen acceptors are $C_1$–$C_{25}$ phosphines, $C_1$–$C_{25}$ phosphites, alkali metal hypophosphites, hypophosphoric acid, $C_1$–$C_{25}$ alkyl sulfides, or $C_1$–$C_{25}$ N-alkyl-morpholines. More preferred classes of oxygen acceptors are triaryl phosphines, trialkyl phosphines, triarylphosphites, or trialkylphosphites. A highly preferred oxygen acceptor is triphenylphosphine.

Preferably, during the step of deoxygenating, the oxygen acceptor is present in a quantity from about 1.0 to about 3.0 moles per mole of epoxyphytyl derivative.

In preferred embodiments of the step of deoxygenating, the deoxygenating is conducted in the presence of a deoxygenation catalyst. A deoxygenation catalyst is defined for the purposes of this invention as any chemical compound or composition which is capable of increasing the rate or selectivity of deoxygenation, without substantial destruction of the deoxygenation catalyst.

Preferred deoxygenation catalysts comprise substituted rhenium trioxide compounds. Substituted rhenium trioxide compounds comprise a rhenium trioxide functional group having a chemically bonded substituent group. The substituent group can be any chemical atom or compound fragment capable of forming a bond to rhenium or oxygen. The substituent group may also bind the substituted rhenium trioxide compound to other chemical groups, compounds surfaces, or support materials, or solublize them in various solvent media. The substituted rhenium trioxide compound may also be dispersed on a support material.

Suitable support materials for the substituted rhenium trioxide catalyst comprise any solid material which is substantially insoluble in the deoxygenation reaction medium, and is substantially chemically stable under the deoxygenation reaction conditions, and does not interfere with the deoxygenation reaction. Suitable support materials include, but are not limited to carbon, activated charcoal, silica, alumina, titania, zirconia, or a zeolite. Suitable support materials may also include organic polymers which can be chemically bonded to the substituent group of a substituted rhenium trioxide compound.

Preferred substituted rhenium trioxide compounds are compounds of the formula

R—ReO$_3$ wherein R is a hydrocarbyl group comprising an alkyl group, an aryl group, an aralkylgroup, or a substituted cyclopentadienyl group.

Preferred rhenium alkyl groups comprise $C_1$–$C_{20}$ straight, branched, or cyclic alkyl groups. Preferred rhenium aryl groups comprise $C_1$–$C_{20}$ aromatic, substituted aromatic, or hetero-aromatic groups. Phenyl, methoxyphenyl, phenylsulfonate, tolyl, xylyl, and napthyl groups are preferred rhenium alkyl groups.

A methyl group is a highly preferred rhenium alkyl group, and corresponds to methyl rhenium trioxide, $CH_3$—ReO$_3$, a highly preferred deoxygenation catalyst.

In the deoxygenating step, the deoxygenation catalyst, the substituted rhenium trioxide compound, or the methyl rhenium trioxide can be present in a quantity from about 0.0001 to about 5.0 weight percent, relative to the weight of the epoxyphytyl. Preferably, the methyl rhenium trioxide can be present in a quantity from about 0.05 to about 1.0 weight percent.

The deoxygenating step can be carried out in the absence of solvent, or conducted in the presence of at least one solvent, or a mixture of solvents. Preferred solvents for deoxygenating comprise aromatic hydrocarbons, aliphatic hydrocarbons, cycloaliphatic hydrocarbons, aliphatic esters, alkanols, ethers, or water.

The deoxygenating can also be carried out in the presence of a two-phase water/organic solvent system. The two-phase water/organic solvent system can contain at least one phase transfer catalyst. The choice of phase transfer catalyst is not critical and most commonly used phase transfer catalysts are effective. For a discussion of such catalysts, see Dehmlow and Dehmlow, *Phase Transfer Catalysis*, 2$^{nd}$ ed., Verlag Chemie, Deerfield Beach Fla., 1983. In general, quaternary ammonium and phosphonium salts, e.g., halides and hydrogen sulfates containing a total of about 8 to about 64 carbon atoms, preferably about 10 to 36 carbon atoms perform well. These salts include tetrabutylammonium hydrogen sulfate, tetrabutylammonium bromide, tricapryl(methyl)ammonium chloride (available under the tradename "Aliquat 336"), benzyl(trimethyl)ammonium chloride, bromide, or iodide, tributylhexadecylphosphonium bromide, ethyltriphenylphosphonium bromide, tetrabutylphosphonium chloride, and the like.

Certain non-ionic phase transfer catalysts are known and may also be used for promoting the deoxygenation step in two-phase water/organic solvent systems. Examples of such non-ionic phase transfer catalysts include crown ethers such as 18-crown-6, dicyclohexyl-18-crown-6, and the like, and also certain polymeric catalysts such as poly(ethylene glycol) and its ethers. These catalysts and many other suitable ones are discussed by the Dehmlow and Dehmlow publication.

Preferred phase transfer catalysts contain about 12 to 36 carbon atoms and have the general formula

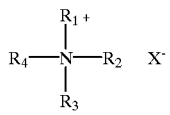

wherein $R_1$, $R_2$, $R_3$, and $R_4$ are the same or different and are selected from alkyl, aryl, or benzyl groups of up to about 18 carbon atoms, and $X^-$ is an anion, e.g. $Cl^-$, $Br^-$, $I^-$, $F^-$, $HSO_4^-$, etc.

The amount of phase transfer catalyst should be chosen so as to give a convenient reaction time and temperature, but the specific amount will vary with the identity of the phase transfer catalyst, the organic solvent, substrates, reactant concentrations, etc. Generally, an effective amount of phase transfer catalyst can be determined by those of average skill in the art without excessive experimentation.

The deoxygenating can occur at temperatures from about $-10°$ C. to about 175° C. Preferably, deoxygenating occurs at a temperature from about 80° C. to about 120 ° C.,. The reaction time for deoxygenating varies from about 0.1 hours to about 24 hours, or preferably for a time from about 0.5 hours to about 3 hours.

The step of deoxygenating is itself a novel and unobvious invention, as applied to the epoxyphytyl derivatives provided by the above-described methods. Certain of the epoxyphytl derivatives could nevertheless be provided by alternative methods of synthetic organic chemistry known to those of skill in the art. Therefore, one embodiment of the current invention provides a method for producing a substituted phytene compound, comprising deoxygenating a substituted epoxyphytyl compound, in the presence of at least one oxygen acceptor and at least one deoxygenation catalyst, under conditions and for a time sufficient to produce at least some of a substituted phytene compound; wherein (a) the substituted epoxyphytl compound has the structure

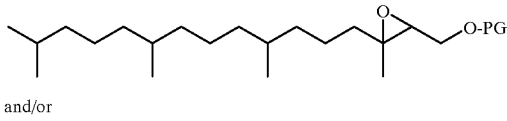

and/or

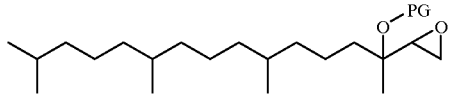

(b) the substituted phytene compound has the structure

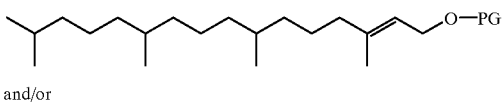

and/or

-continued

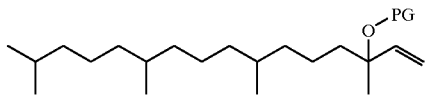

wherein PG is hydrogen, or a removable protecting group. In certain highly preferred embodiments, the substituted epoxyphytyl compound is

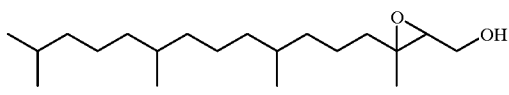

and/or

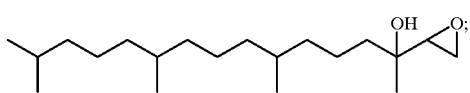

and the substituted phytene compound is

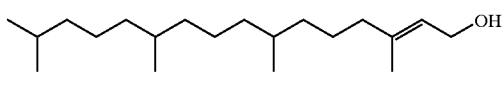

and/or

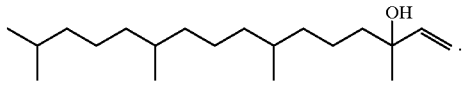

Methods for the Synthesis of Aloha-Tocopherol

The above-described methods provide phytol, isophytol, substituted phytene compounds, phytene derivatives, and isophytene derivatives, which are suitable starting materials for the synthesis of alpha-tocopherol, the most desirable of the Vitamin E series of compounds. Therefore, in certain embodiments, the instant invention provides methods for condensing phytol, isophytol, substituted phytene compounds, phytene derivatives, and isophytene derivatives produced by the above-described methods with trimethylhydroquinone or trimethylhydroquinone derivatives, to provide alpha-tocopherol or certain of it's derivatives.

One method of the invention provides for condensing a trimethylhydroquinone derivative with phytol, isophytol, or a mixture thereof, in the presence of a Lewis acid catalyst, to produce alpha-tocopherol or an alpha-tocopherol derivative. The phytol, isophytol, or a mixture thereof must have been produced by the above described methods. The step of condensing is conducted in the presence of a Lewis acid catalyst, as is known in the art. A preferred Lewis acid catalyst for the step of condensing is zinc chloride.

The class of trimethylhydroquinone derivatives have the structure:

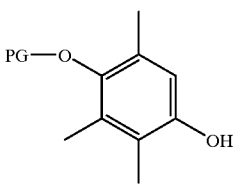

wherein PG is hydrogen or a removable protecting group. Trimethylhydroquinone derivatives include trimethylhydroquinone (where PG=hydrogen).

Alpha-tocopherol derivatives have the structure:

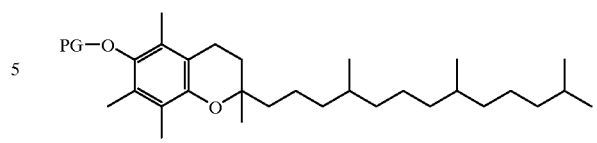

wherein PG is hydrogen or a removable protecting group. Preferred protecting groups include acyl groups derived from $C_2$–$C_{20}$ carboxylic acids. When the acyl group of a carboxylic acid is bonded to the oxygen atom of an epoxygeranylgeraniol derivative, a $C_2$–$C_{20}$ ester protecting group is formed. Acetate ester protecting groups, derived from the acyl portion of acetic acid, acetyl halides, acetic anhydride, ketene, methyl acetate, or ethyl acetate are particularly preferred ester protecting groups. Alpha-tocopherol derivatives include Alpha-tocopherol (where PG=hydrogen).

In an alternative embodiment, the invention provides a method for producing alpha-tocopherol, comprising the steps of:

(a) providing an epoxyphytyl derivative;

(b) deoxygenating the epoxyphytyl derivative in the presence of an oxygen acceptor and a deoxygenation catalyst to produce phytol, a phytene derivative, isophytol, an isophytene derivative, or a mixture thereof; and (c) condensing the phytol, phytene derivative, isophytol, isophytene derivative, or a mixture thereof with trimethylhydroquinone;

to produce alpha-tocopherol.

In this embodiment, the epoxyphytyl derivative can be provided by any method, but the steps of deoxygenating and condensing are carried out by methods described above. In a preferred embodiment, the epoxyphytyl derivative is a substituted epoxyphytyl compound, the phytene derivative is a substituted phytene compound, and the isophytene derivative is a substituted phytene compound. In a more highly preferred embodiment, the epoxyphytyl derivative is 2,3-epoxyphytol, the phytene derivative is phytol, and the isophytene derivative is isophytol.

In a highly preferred embodiment, the invention provides a method for converting geranylgeraniol to alpha-tocopherol, comprising the steps of:

(a) epoxidizing geranylgeraniol in the presence of an organic hydroperoxide and a molybdenum or vanadium catalyst, to produce 2,3-epoxy-geranylgeraniol;

(b) hydrogenating 2,3-epoxy-geranylgeraniol in the presence of a hydrogenation catalyst to produce 2,3-epoxyphytol;

(c) deoxygenating 2,3-epoxyphytol in the presence of a phosphine and $CH_3$—$ReO_3$, to produce phytol, isophytol, or mixtures thereof; and (d) condensing trimethylhydroquinone with phytol, isophytol, or mixtures thereof, in the presence of a Lewis acid catalyst;

to produce alpha-tocopherol.

Experimental

The following examples are put forth so as to provide those of ordinary skill in the art with a complete disclosure and description of how the compounds, compositions, and methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.)

But some errors and deviations should be accounted for. Unless indicated otherwise, parts are parts by weight, temperature is in ° C. or is at ambient temperature, and pressure is at or near atmospheric.

EXAMPLE 1

This example illustrates the production of 2,3-epoxy-geranylgeraniol, wherein the epoxidation is conducted in toluene using tert-butylhydroperoxide in the presence of vanadium.

A solution of 5.0 grams of geranylgeraniol (0.0172 mole) in 25 ml of toluene was treated with 50 mg of vanadium tris(acetylacetonate) (0.8 mole %) and stirred at reflux under nitrogen. 5.76 ml of 3.3 molar tert-butylhydroperoxide in toluene (0.019 mole) was added dropwise. At the end of the addition, heating was discontinued and the mixture was allowed to cool to room temperature. Analysis by thin layer chromatography disclosed complete conversion of starting material to a single product. The reaction mixture was treated with about 50 ml of about 5% aqueous sodium sulfite solution, stirred 10 minutes and decanted. The organic phase was washed with water, 5% $NaHCO_3$, brine, and dried over $MgSO_4$. Removal of solvent under reduced pressure afforded 5.28 g (98%) of pale yellow oily product. NMR analysis supported the desired structure of 2,3-epoxygeranylgeraniol.

EXAMPLE 2

This example illustrates the production of epoxyphytol by hydrogenation of 2,3-epoxy-geranylgeraniol.

The total product from Example 6 was dissolved in 50 ml of ethanol, treated with 0.2 gram of 5% palladium on carbon catalyst, and hydrogenated at 1 atm $H_2$ for 72 hrs. (treatment for about 4 hrs at 40 psi $H_2$, 40° C. is more convenient). The mixture was filtered (celite) and stripped of solvent to give 5.03 gram (95%) product as a colorless oil, identical by chromatography and NMR spectroscopy with an authentic sample of epoxyphytol prepared by epoxidation of phytol.

EXAMPLE 3

This example illustrates the preparation of a phytol/isophytol mixture from epoxyphytol. A solution of 5.0 grams of epoxyphytol (0.016 mole) from Example 7 and 4.72 grams of triphenylphosphine (0.018 mole) in 50 ml of toluene was treated with 80 mg of methylrhenium trioxide and stirred under reflux for two hours. Thin layer chromatography analysis indicated the absence of starting material and the presence of isophytol, phytol, and a trace of front-running olefins. The mixture was cooled, filtered through a small pad of silica gel to remove catalyst, and stripped of solvent to give 5.0 grams of crude product. Silica gel chromatography afforded 0.4 grams of phytadienes (7.4%) and 3.9 grams (83%) of a 3:1 mixture of isophytol and phytol.

Subsequent runs of this experiment were conducted using less catalyst (20–40 mg) and catalyst removal by washing with aqueous sodium carbonate solution (the yellow hydrolysis product $ReO_4^-$ goes into the water layer immediately). Crude products from this procedure were essentially free of phytadienes (nmr, vpc). Distillation gave the phytol/isophytol mixture in greater than 90% yield.

Throughout this application, various publications are referenced. The disclosures of these publications in their entireties are hereby incorporated by reference into this application in order to more fully describe the state of the art to which this invention pertains.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method comprising the steps of:
   (a) oxidizing geranylgeraniol or a geranylgeraniol derivative to produce an epoxy-geranylgeraniol derivative;
   (b) reducing the epoxy-geranylgeraniol derivative to produce an epoxyphytyl derivative; and
   (c) deoxygenating the epoxyphytyl derivative in the presence of at least one oxygen acceptor;
   to produce phytol, a phytene derivative, isophytol, an isophytene derivative, or a mixture thereof.

2. The method of claim 1, wherein the epoxy-geranylgeraniol derivative comprises 2,3-epoxy-geranylgeraniol, 1,2-epoxy-geranylgeraniol, or a mixture thereof; and the epoxyphytol derivative comprises 2,3-epoxy-epoxyphytol, 1,2-epoxy-isophytol, or a mixture thereof.

3. The method of claim 1, wherein the step of oxidizing is carried out in the presence of at least one oxidizing agent.

4. The method of claim 1, wherein the oxidizing comprises epoxidizing in the presence of at least one epoxidation catalyst.

5. The method of claim 4, wherein the epoxidation catalyst comprises a vanadium or molybdenum compound.

6. The method of claim 4, wherein the step of epoxidizing is carried out in the presence of an organic hydroperoxide.

7. The method of claim 4, wherein the step of epoxidizing is carried out in the presence of hydrogen peroxide, t-butyl hydroperoxide or cumene hydroperoxide.

8. The method of claim 4, wherein the epoxidizing is carried out in the presence of at least one solvent.

9. The method of claim 8, wherein the solvent is an aromatic hydrocarbon, an aliphatic hydrocarbon, a cycloaliphatic hydrocarbon, or an aliphatic ester.

10. The method of claim 1, wherein the step of reducing comprises hydrogenating in the presence of a hydrogenation catalyst and a hydrogen donor.

11. The method of claim 10, wherein the hydrogenation catalyst comprises Raney nickel, palladium on carbon, platinum on carbon, or platinum oxide.

12. The method of claim 10, wherein the hydrogenation catalyst comprises at least one transition metal, transition metal salt, transition metal complex, or a mixture thereof.

13. The method of claim 12, wherein the transition metal, transition metal salt, or transition metal complex comprises chromium, molybdenum, tungsten, manganese, rhenium, iron, ruthenium, osmium, cobalt, rhodium, iridium, nickel, palladium, platinum, or copper.

14. The method of claim 12, wherein the transition metal, transition metal salt, or transition metal complex is disposed on the surfaces of a support material.

15. The process of claim 14, wherein the transition metal, transition metal salt, or transition metal complex comprises from about 0.1 to about 10 weight percent of the catalyst.

16. The process of claim 14, wherein the support material comprises carbon, charcoal, silica, alumina, titania, zirconia, a zeolite, barium sulfate, or calcium sulfate.

17. The method of claim 10, wherein the hydrogenation catalyst is present in a quantity of from about 0.001 to about 10 weight percent based on the starting weight of epoxygeranylgeraniol.

18. The method of claim 10, wherein the hydrogenating comprises transfer hydrogenating.

19. The method of claim 10, wherein the hydrogen donor comprises $H_2$ gas at a pressure from about 1 atmosphere to about 200 atmospheres.

20. The method of claim 10, wherein the hydrogenating is performed at a temperature from about 0° C. to about 150° C.

21. The method of claim 10, wherein the hydrogenating is conducted in the presence of at least one solvent.

22. The method of claim 1, wherein the deoxygenating is conducted in the presence of a deoxygenation catalyst.

23. The method of claim 22, wherein the deoxygenation catalyst comprises a substituted rhenium trioxide compound.

24. The method of claim 22, wherein the deoxygenation catalyst comprises $CH_3$—$ReO_3$.

25. The method of claim 22, wherein the oxygen acceptor comprises a phosphine, a phosphite, an alkali metal hypophosphite, hypophosphoric acid, an alkyl sulfide or an N-alkylmorpholine.

26. The method of claim 22 wherein the oxygen acceptor is triphenylphosphine.

27. A substituted epoxyphytyl compound of the structure

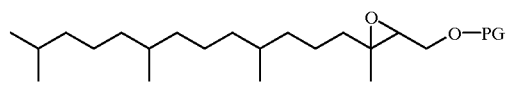

and/or

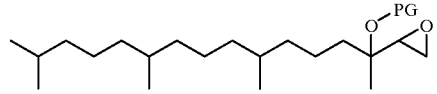

wherein PG is an acyl group derived from $C_2$–$C_{20}$ carboxylic acid.

28. A method for producing a substituted phytene compound, comprising deoxygenating a substituted epoxyphytyl compound, in the presence of at least one oxygen acceptor and at least one deoxygenation catalyst, under conditions and for a time sufficient to produce at least some of a substituted phytene compound; wherein (a) the substituted epoxyphytl compound has the structure

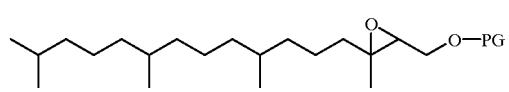

and/or

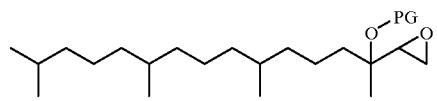

(b) the substituted phytene compound has the structure

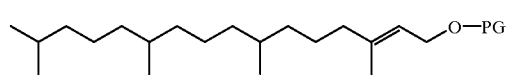

and/or

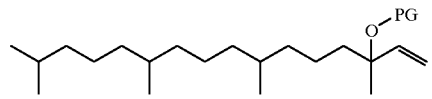

wherein PG is hydrogen, or a removable protecting group.

29. The method of claim 28, wherein the substituted epoxyphytyl compound is

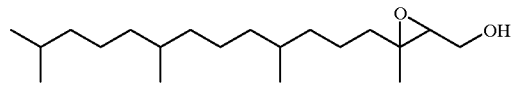

and/or

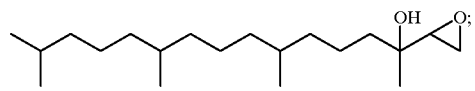

and the substituted phytene compound is

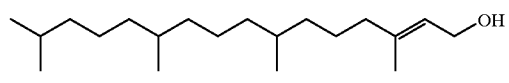

and/or

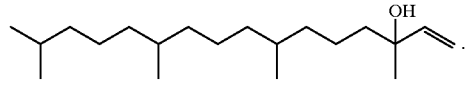

30. The method of claim 28, wherein the deoxygenation catalyst is a substituted rhenium trioxide compound.

31. The method of claim 30, wherein the substituted rhenium trioxide catalyst is dispersed on the surface of a support material.

32. The method of claim 31, wherein the support material comprises carbon, activated charcoal, silica, alumina, titania, zirconia, a zeolite, barium sulfate, or calcium sulfate.

33. The method of claim 31, wherein the substituted rhenium trioxide catalyst is bonded to an organic polymer or a support material.

34. The method of claim 31, wherein the substituted rhenium trioxide compound is a compound of the formula $$R—ReO_3$$

and R is a hydrocarbyl group comprising an alkyl group, an aryl group, an aralkyl group, a cyclopentadienyl group, or a substituted cyclopentadienyl group.

35. The method of claim 28 wherein the deoxygenation catalyst is $CH_3$—$ReO_3$.

36. The method of claim 30, wherein the substituted rhenium trioxide compound is present in a quantity from about 0.0001 to about 5.0 weight percent, relative to the weight of the substituted epoxyphytyl compound.

37. The method of claim 28, wherein the oxygen acceptor comprises a phosphine, a phosphite, an alkali metal hypophosphite, hypophosphoric acid, an alkyl sulfide, or an N-alkylmorpholine.

38. The method of claim 28, wherein the oxygen acceptor comprises a triarylphosphine, a trialkylphosphine, a triarylphosphite, or a trialkylphosphite.

39. The method of claim 28, wherein the oxygen acceptor comprises triphenylphosphine.

40. The method of claim 28, wherein the oxygen acceptor is present in a quantity from about 1.0 to about 3.0 moles per mole of substituted epoxyphytyl compound.

41. The method of claim 28, wherein the deoxygenating is conducted in the presence of at least one solvent.

42. The method of claim 28, wherein the deoxygenating is conducted in the presence of a two-phase water/organic solvent system.

43. The method of claim 42, wherein the two-phase water/organic solvent system contains at least one phase transfer catalyst.

44. The method of claim 28, wherein deoxygenating occurs at a temperature from about −10° C. to about 175° C., for a time from about 0.1 hours to about 24 hours.

45. The method of claim 28, wherein deoxygenating occurs at a temperature from about 80° C. to about 120° C., for a time from about 0.5 hours to about 3 hours.

46. The method of claim 1, further comprising condensing a trimethylhydroquinone derivative with phytol, isophytol, or a mixture thereof, in the presence of a Lewis acid catalyst, to produce alpha-tocopherol or an alpha-tocopherol derivative.

47. A method for producing alpha-tocopherol, comprising the steps of:
   (a) providing an epoxyphytyl derivative;
   (b) deoxygenating the epoxyphytyl derivative in the presence of an oxygen acceptor and a deoxygenation catalyst to produce phytol, a phytene derivative, isophytol, an isophytene derivative, or a mixture thereof; and
   (c) condensing the phytol, phytene derivative, isophytol, isophytene derivative, or a mixture thereof with trimethylhydroquinone;
   to produce alpha-tocopherol.

48. The method of claim 47, wherein the epoxyphytyl derivative is a substituted epoxyphytyl compound, the phytene derivative is a substituted phytene compound, and the isophytene derivative is a substituted phytene compound.

49. The method of claim 47, wherein the condensing is conducted in the presence of a Lewis acid catalyst.

50. The method of claim 47, wherein the condensing is conducted in the presence of zinc chloride.

51. A method for converting geranylgeraniol to alpha-tocopherol, comprising the steps of:
   (a) epoxidizing geranylgeraniol in the presence of an organic hydroperoxide and a molybdenum or vanadium catalyst, to produce 2,3-epoxy-geranylgeraniol;
   (b) hydrogenating 2,3-epoxy-geranylgeraniol in the presence of a hydrogenation catalyst to produce 2,3-epoxyphytol;
   (c) deoxygenating 2,3-epoxyphytol in the presence of a phosphine and $CH_3$—$ReO_3$, to produce phytol, isophytol, or mixtures thereof; and
   (d) condensing trimethylhydroquinone with phytol, isophytol, or mixtures thereof, in the presence of a Lewis acid catalyst;
   to produce alpha-tocopherol.

* * * * *